United States Patent [19]

Ohoka et al.

[11] Patent Number: 4,844,298

[45] Date of Patent: Jul. 4, 1989

[54] APPARATUS FOR AUTOMATICALLY DISPENSING ACCURATELY A PREDETERMINED QUANTITY OF LIQUIDS REQUIRED TO BE STORED AT CONSTANT TEMPERATURES

[75] Inventors: Akihiro Ohoka; Kouichi Washimi, both of Osaka, Japan

[73] Assignee: Sumitomo Electric Industries, Ltd., Osaka, Japan

[21] Appl. No.: 166,508

[22] Filed: Mar. 10, 1988

[30] Foreign Application Priority Data

Mar. 11, 1987 [JP] Japan .............................. 62-35523[U]
May 29, 1987 [JP] Japan ................................ 62-134716
Jun. 13, 1987 [JP] Japan ................................ 62-147313

[51] Int. Cl.$^4$ ............................................. B67D 5/14
[52] U.S. Cl. ...................................... 222/58; 222/63; 222/108; 222/330; 222/276; 141/104; 141/243
[58] Field of Search ................. 141/104, 237, 242–244; 73/863.01, 863.31, 863.32; 222/58, 56, 61, 108, 254–255, 266, 330–331, 333, 63, 276; 422/100

[56] References Cited

U.S. PATENT DOCUMENTS

| | | | |
|---|---|---|---|
| 2,765,962 | 10/1956 | Perkins | 222/255 |
| 3,666,420 | 5/1972 | Paatzsch | 141/104 X |
| 4,199,013 | 4/1980 | Reich et al. | 222/135 X |
| 4,478,094 | 10/1984 | Salomaa et al. | 73/863.32 |
| 4,554,839 | 11/1985 | Hewett et al. | 73/864.16 |
| 4,728,501 | 3/1988 | Atake | 422/100 |

Primary Examiner—Michael S. Huppert
Attorney, Agent, or Firm—Cushman, Darby & Cushman

[57] ABSTRACT

Apparatus for automatically dispensing accurately a predetermined quantity of a liquid required to be stored at room temperature including a syringe pump, a liquid tank, and a pump displacement mechanism for moving the syringe pump between the liquid tank and a container. The piston of the syringe pump is displaced by a piston displacement mechanism. A weigher measures weights of the tank and liquid in the tank as well as a draining system for draining the liquid of the liquid tank. Liquid is supplied to the liquid tank from a supply system. A control device controls displacement of the syringe pump and the piston of the syringe pump, actuation of the supply system and the drainage system, and reads measurement output signals of the weigher.

9 Claims, 10 Drawing Sheets

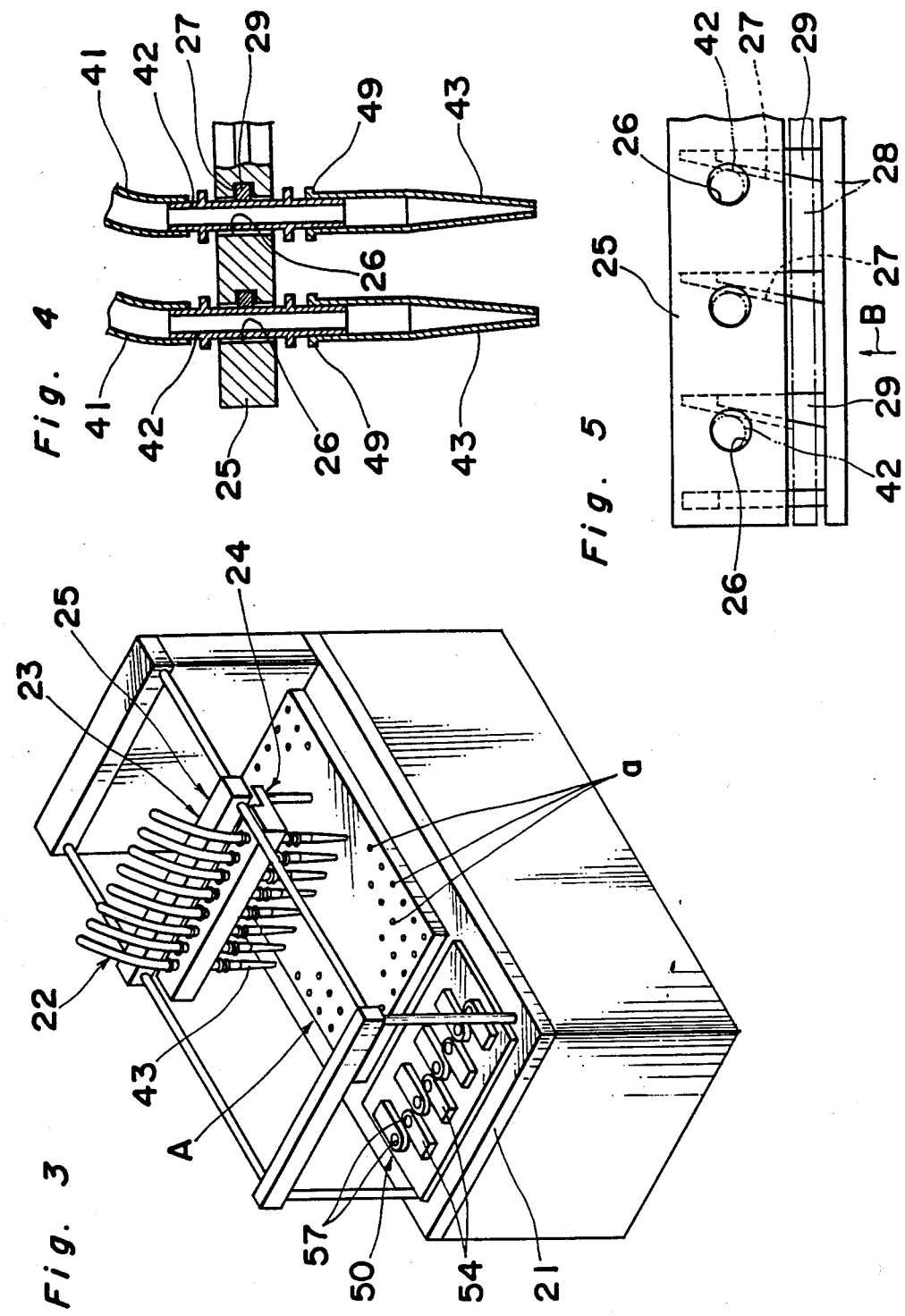

Fig. 12
Fig. 13
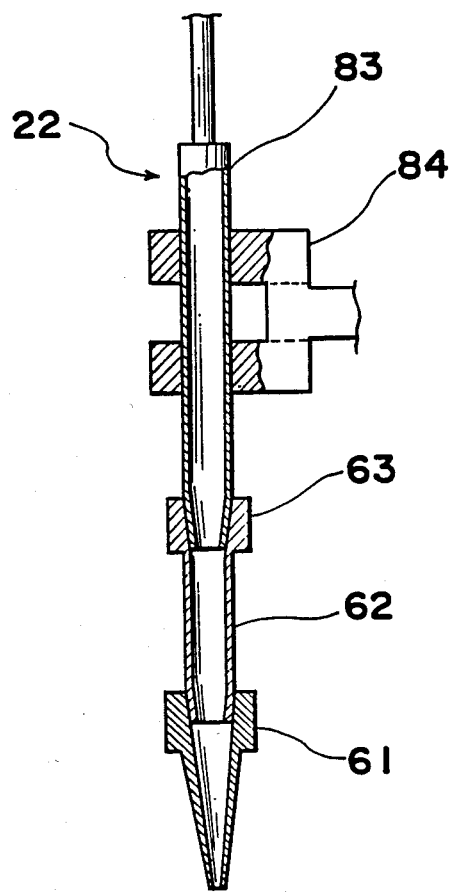
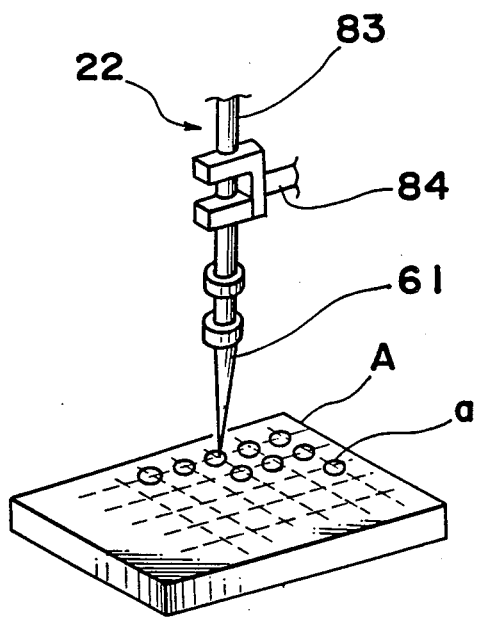

APPARATUS FOR AUTOMATICALLY DISPENSING ACCURATELY A PREDETERMINED QUANTITY OF LIQUIDS REQUIRED TO BE STORED AT CONSTANT TEMPERATURES

BACKGROUND OF THE INVENTION

The present invention relates to an automatic dispensing machine for automatically dispensing accurately a predetermined quantity of liquids required to be stored at a constant temperature. The present invention is also applicable to an automatic inspection machine utilizing reagents, etc. and an automatic incubator in which culture solutions, etc. are dispensed.

Conventionally, in dispensing machines, it has been so arranged as shown in FIG. 1 that liquid in a liquid tank 2 enclosed by a constant temperature bath 1 is directly dispensed into a container 4 by using a discharge pump 3. A dispensing quantity of the liquid set at this time is controlled on the basis of an operating time of the discharge pump 3. Meanwhile, a tube 5 extending from the liquid tank 2 to the container 4 through the discharge pump 3 is empty at the time of start of dispensing of the liquid. Therefore, in order to fill the tube 5 with the liquid prior to start of dispensing of the liquid of the liquid tank 2, a discharge opening 6 is required to be displaced to a waste liquid container 8 by a displacement mechanism 7 such that the liquid is discharged from the discharge opening 6 into the waste liquid container 8.

In the known dispensing machines, the liquid of the liquid tank 2 is directly dispensed into the container 4 by the discharge pump 3 and the dispensing quantity of the liquid is controlled based on the operating time of the discharge pump 3. Thus, the known dispensing machines have such drawbacks that the dispensing quantity of the liquid changes due to deterioration of the tube 5 or according to presence or absence of droplets at the discharge opening 6 and that the tube 5 is fractured due to defective setting of the tube 5, thereby resulting in excessive reduction of the dispensing quantity of the liquid.

Furthermore, in the known dispensing machines, since the tube 5 is empty at the time of start of dispensing of the liquid, the tube 5 is required to be filled with the liquid initially. In the known automatic dispensing machines in which the liquid is drawn into the waste liquid container 8 before the liquid is dispensed into the container 4, an operator cannot judge whether the tube 5 has been filled with the liquid. Therefore, the known automatic dispensing machines have such a disadvantage that dispensing of the liquid into the container 4 should be started after the liquid has been sufficiently delivered into the waste liquid tank 8, thus resulting in increase of waste of the liquid.

Meanwhile, in response to recent progress in study of biotechnology, automatic culture processing apparatuses for efficiently culturing microorganisms have been developed greatly. In culture of microorganisms, either cells to be cultured or bacteria to be cultured and culture solution are usually introduced into a number of wells arranged in a pattern of a matrix on a tray and then, the wells are covered by a lid such that proliferation of the cells or the bacteria is effected in a temperature controlled room for a certain time period. During proliferation of the microorganisms, replenishment, exchange or change of the culture solution is necessary.

To this end, in the prior art automatic culture processing apparatuses, a plurality of pipets are moved upwardly and downwardly by a lifting mechanism and tips of the pipets are inserted into the wells such that exchange of the culture solution, i.e. suction and discharge of the culture solution are performed. For example, wells arranged in a pattern of an 8×12 matrix, namely 8 (number of rows of the matrix) wells in a sidewise direction of the tray and 12 (number of columns of the matrix) wells arranged in a longitudinal direction of the tray are provided on a tray in common use. In this case, 8 pipets corresponding to the 8 wells in the sidewise direction of the tray are provided so as to be moved horizontally in one direction by a drive mechanism such that replenishment, exchange or change of the culture solution is performed at all the wells.

However, the above described exchange, etc. of the culture solution is not always performed at all the wells. Namely, in the case where germs have been mixed into a specific one of the wells in the course of culture of the microorganisms, germicide is syringed into the specific well and the culture solution is not required to be discharged into the specific well by inserting thereinto the pipet in the subsequent exchange, etc. of the culture solution. On the contrary, it is necessary to prevent the germicide from attaching to the pipet through insertion of the pipet into the specific well.

However, the prior art automatic culture processing apparatuses provided with a plurality of the pipets has been disadvantageous in that since exchange, etc. of the culture solution is performed at the wells of one row or one column of the matrix simultaneously, the pipets cannot be used if there exists a well having germs mixed thereinto.

Furthermore, in the prior art automatic culture processing apparatuses, exchange, etc. of the culture solution are performed by inserting the tips of the pipets into the wells, the tips are brought into contact with the culture solution in the wells, so that such a problem arises that if the identical pipets are used, transfer of germs, etc. among the wells or between the trays occurs. Therefore, in order to obviate such a problem, a detachable tip is provided at a distal end of each of the pipets such that contamination of the culture solution by the germs is prevented through exchange of the tips. Since a long time period is required for exchange of the tips and the distal end of each of the pipets may be bent if the tips are exchanged manually, it is desirable to automate exchange of the tips. For example, in the case of the wells arranged in a pattern of a 8×12 matrix, not only the tray or the pipets should be moved horizontally but the pipets should be moved vertically in order to gain access to the wells. Thus, generally, when automatic culture processing apparatuses are of a type in which the pipets are moved horizontally, it is desirable that a movable portion is reduced in weight so as to decrease power consumption for driving the movable portion and a tip exchange mechanism is both light in weight and simple in construction at the movable side. However, such automatic culture processing apparatuses are not known at present.

SUMMARY OF THE INVENTION

Accordingly, an essential object of the present invention is to provide a dispensing machine which is capable of accurately dispensing a predetermined quantity of liquid and reduces waste of the liquid in dispensing of the liquid, with substantial elimination of the disadvantages inherent in conventional dispensing machines of this kind.

Another important object of the present invention is to provide a dispensing machine of the above described type which is provided with a pipet selection device for enabling selective actuation of a plurality of pipets employed in the dispensing machine.

Still another object of the present invention is to provide a dispensing machine of the above described type which is further provided with a tip exchange device light in weight and simple in construction.

BRIEF DESCRIPTION OF THE DRAWINGS

These and other objects and features of the present invention will become apparent from the following description taken in conjunction with the preferred embodiment thereof with reference to the accompanying drawings, in which:

FIG. 3 is a perspective view of a pipet selection device employable in the dispensing machine of FIG. 2;

FIG. 4 is a fragmentary sectional view of a pipet holding mechanism of the pipet selection device of FIG. 3;

FIG. 5 is a fragmentary top plan view of the pipet holding mechanism of FIG. 4;

FIG. 12 is a sectional view of a distal end of a pipet of the tip exchange device of FIG. 10;

FIG. 13 is a perspective view of the pipet of FIG. 12;

Before the description of the present invention proceeds, it is to be noted that like parts are designated by like reference numerals throughout several views of the accompanying drawings.

DETAILED DESCRIPTION OF THE INVENTION

Figure 1:
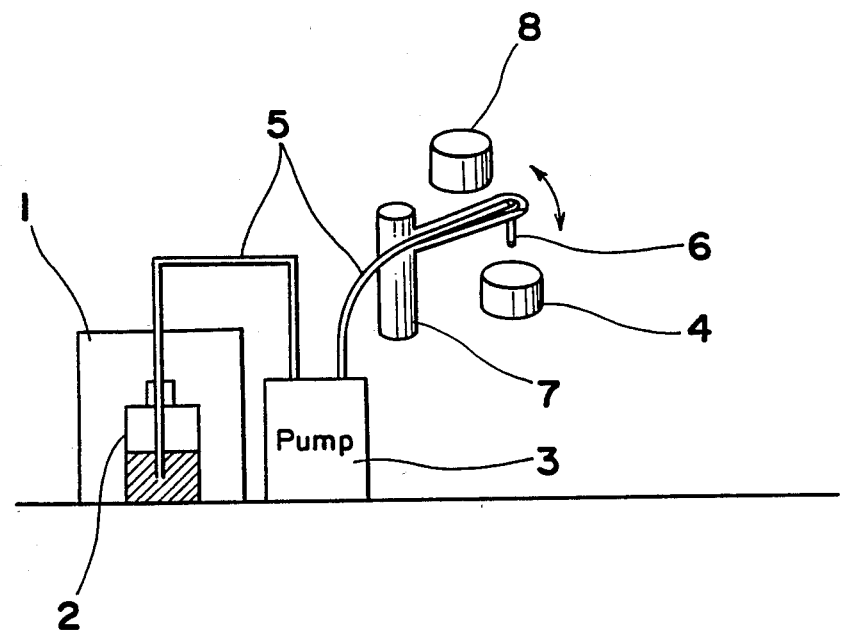
FIG. 1 is a schematic view of a prior art dispensing machine (already referred to)
Figure 2:
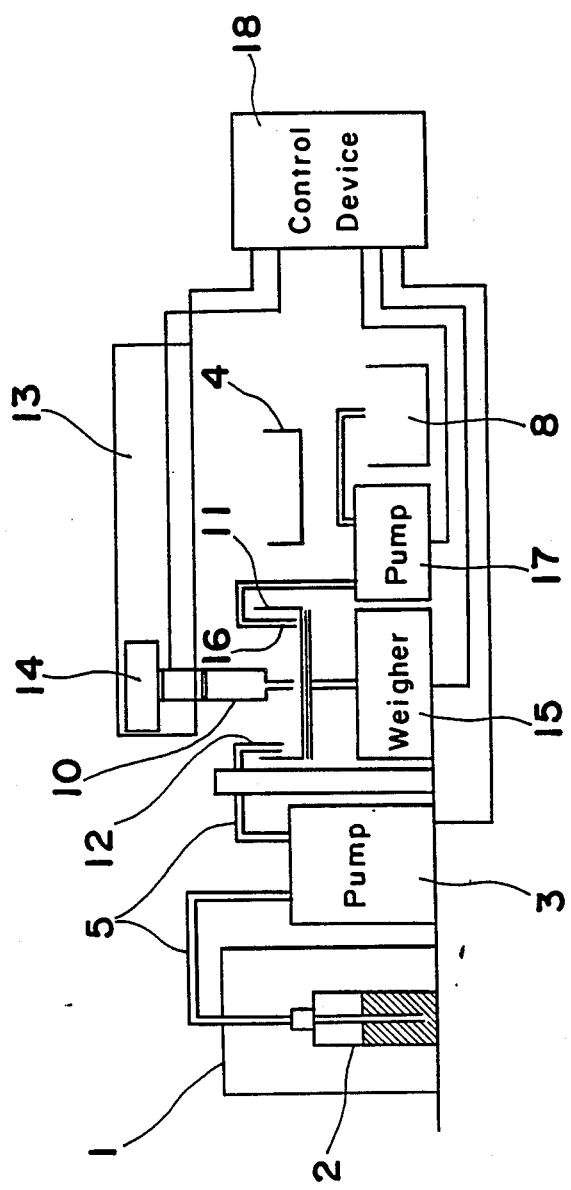
FIG. 2 is a schematic view of a dispensing machine according to the present invention.

Referring now to the drawings, there is shown in FIG. 2, a dispensing machine according to the present invention. The dispensing machine includes a syringe pump 10, a liquid tank 11, a discharge pipe 12, a pump displacement mechanism 13 for displacing the syringe pump 10 between the liquid tank 11 and a container 4, a piston driving mechanism 14 for driving a piston of the syringe pump 10, a weigher 15 for measuring weights of the liquid tank 11 and liquid contained in the liquid tank 11, a drainage pipe 16 for draining the liquid of the liquid tank 11, a drainage pump 17 for draining the liquid of the liquid tank 11, a waste liquid container 8, a liquid tank 2 for containing supplied liquid and a constant temperature bath 1 for maintaining the liquid in the liquid tank 2 at a constant temperature.

The dispensing machine further includes a discharge pipe 12 for discharging the liquid of the liquid tank 2 into the liquid tank 11, a discharge pump 3 for discharging the liquid of the liquid tank 2 into the liquid tank 11, a tube 5 extending from the liquid tank 2 to the liquid tank 11 and a control device 18. The control device 18 controls displacement of the syringe pump 10 and the piston of the syringe pump 10 and actuation of the discharge pump 3 and the drainage pump 17 and reads measurement output signals of the weigher 15.

Hereinbelow, operation of the dispensing machine is described. Initially, the supplied liquid is stored in the liquid tank 2 enclosed by the constant temperature bath 1. In response to a signal from the control device 18, the discharge pump 3 is actuated so as to discharge the liquid of the liquid tank 2 into the liquid tank 11. At this time when the liquid tank 11 is empty, the weigher 15 measures weight of the liquid tank 11 and the control device 18 reads the measured value of the weigher 15. During discharge of the liquid of the liquid tank 2 into the liquid tank 11, the weigher 15 measures weight of the liquid tank 11 at a predetrmined interval and detects weight of the liquid by subtracting the weight of the empty liquid tank 11 from the total weight of the empty liquid tank 11 and the liquid. When a necessary quantity of the liquid has been discharged into the liquid tank 11, the control device 18 stops actuation of the discharge pump 3.

In order to dispense the liquid of the liquid tank 11 into the container 4, the syringe pump 10 is lowered to a suction position for the liquid tank 11 by the pump displacement mechanism 13. Then, the piston of the syringe pump 10 is driven by the piston driving mechanism 14 so as to suck a necessary quantity of the liquid from the liquid tank 11. Subsequently, the syringe pump 10 is lifted to a discharge position for the container 4 by the pump displacement mechanism 13 so as to discharge the liquid into the container 4 upon drive of the piston of the syringe pump 10. The piston of the syringe pump 10 is driven through its positional control and thus, it becomes possible to control a dispensed quantity of the liquid by controlling a travel distance of the piston of the syringe pump 10.

The control device 18 actuates the drainage pump 17 such that the liquid remaining in the liquid tank 11 is drained into the waste liquid container 8 through the drainage pipe 16 by the drainage pump 17.

Furthermore, in the dispensing machine, it is possible to detect malfunctions of the dispensing machine such as damage or fracture of the tube 5 and failure of the pumps by monitoring the output signals of the weigher 15.

As is clear from the foregoing description in the dispensing machine of the present invention, since a predetermined quantity of the liquid can be accurately dispensed into the container and waste of the liquid is reduced, the dispensing machine can be applicable to an inspection machine utilizing expensive reagents, etc. or an incubator in which expensive cell solutions, etc. are dispensed.

Furthermore, in the dispensing machine of the present invention, since malfunctions such as deterioration of the tube, defective connection of the tube, failure of the pumps, etc. can be detected by monitoring the output signals of the weigher, the dispensing machine can be effectively applied to automatic apparatuses.

FIGS. 3 to 9 show a pipet selection device which can be employed in the dispensing machine of the present invention. In FIG. 3, a horizontal displacement mechanism 23 for displacing a plurality of pipets 22 horizontally and a lifting mechanism 24 for moving the pipets 22 upwardly and downwardly are provided above a base plate 21 for supporting a rectangular culture tray A. A plurality of wells a are arranged in a pattern of a matrix on the culture tray A. The pipets 22 are so provided as to correspond, in number, to the wells a of a sidewise direction of the culture tray A and are supported by a support member 25 such that the support member 25 is moved in one horizontal direction and in a vertical direction by the horizontal displacement mechanism 23 and the lifting mechanism 24, respectively. In FIG. 3, since the wells a are arranged in a pattern of an 8×12 matrix on the culture tray A, 8 pipets 22 are provided.

As shown in FIG. 4, each of the pipets 22 is constituted by a flexible pipe 41 for sucking and supplying liquid, a rectilinear slide pipe 42 connected with one end of the flexible pipe 41 and a tip 43 attached detachably to a lower end of the slide pipe 42. On the other hand, as shown in FIGS. 4 and 5, a plurality of through-holes 26 corresponding to the wells a of the sidewise direction of the culture tray A, respectively are formed on the support member 25. The slide pipe 42 is loosely fitted through each of the through-holes 26 such that the through-holes 26 act as slide guides for the pipets 22, respectively. Furthermore, a plurality of apertures or slots 27 each for inserting thereinto a wedged holder 29 for holding each of the pipets 22 are formed in the support member 25 and extend from one side of the support member 25 so as to partially open into the through-holes 26, respectively. The holders 29 coupled with a connecting rod 28 are drawably inserted into the apertures 27, respectively.

In the above described pipet holding mechanism, the connecting rod 28 is thrusted by a proper drive means (not shown) so as to push the holders 29 into the apertures 27, respectively in the direction of the arrow B in FIG. 5. Thus, a wedged face of each of the holders 29 is projected into each of the through-holes 26 so as to depress the slide pipe 42 into pressing contact with a face of each of the through-holes 26 as shown in the one-dot chain lines of FIG. 5 such that the slide pipe 42 is secured in each of the through-holes 26 by each of the holders 29.

On the other hand, when the holders 29 have been drawn from the apertures 27, respectively, each of the holders 29 is disengaged from the slide pipe 42 and thus, the pipets 22 can be again slid upwardly and downwardly in the through-holes 26, respectively. Therefore, at this time, height of the tip 43 can be adjusted arbitrarily within a permissible travel stroke of the slide pipe 42.

Figure 6:
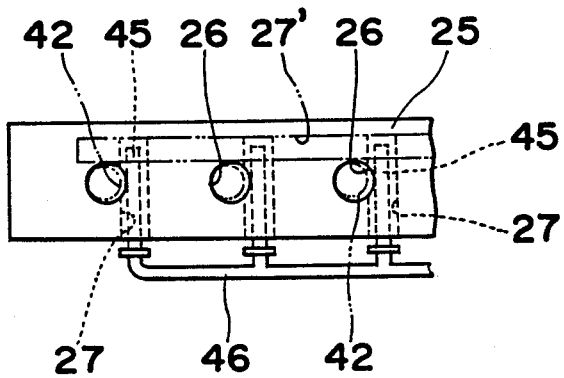
FIG. 6 is a view similar to FIG. 5, particularly showing a modification thereof.
Figure 7:
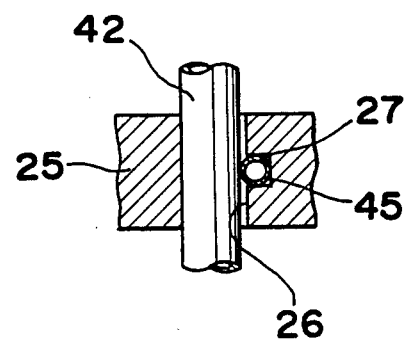
FIG. 7 is a sectional view of the modified pipet holding mechanism of FIG. 6.

FIGS. 6 and 7 show a modification of the pipet holding mechanism of FIGS. 4 and 5. In this modified pipet holding mechanism, elastic tubes 45 each having one closed end are, respectively, inserted into the apertures 27 formed in the support member 25 and are connected with a tube 46 for supplying pressurized fluid to the elastic tubes 2. Upon supply of the pressurized fluid from the tube 46 to the elastic tubes 45, the elastic tubes 45 are expanded so as to become larger in diameter such that the slide pipe 42 is depressed against the face of each of the through-holes 26 by each of the elastic tubes 45 as shown in FIG. 7. Therefore, in this modified pipet holding mechanism, fine adjustments of a holding force of the pipets 22 can be performed more easily than in the pipet holding mechanism of FIGS. 4 and 5 employing the wedged holders 29. Furthermore, it can also be so arranged as shown by the one-dot chain lines in FIG. 6 that a bore 27' extending in a longitudinal direction of the support member 25 is formed in the support member 25 so as to open into the through-holes 26 and a long elastic tube having one closed end is inserted into the bore 27' such that all the slide pipes 42 are simultaneously held through expansion and contraction of this elastic tube.

Figure 8:
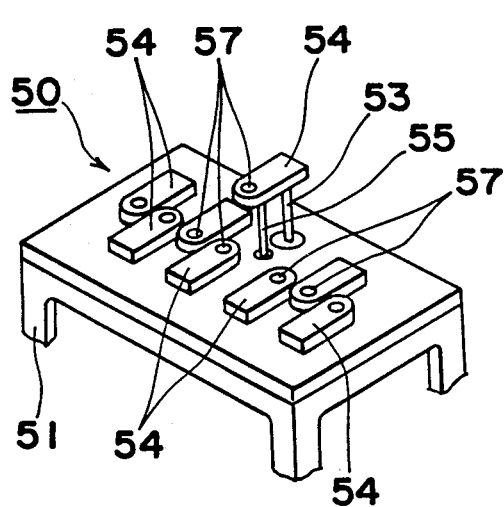
FIG. 8 is a perspective view of a stopper mechanism of the pipet selection device of FIG. 3.
Figure 9:
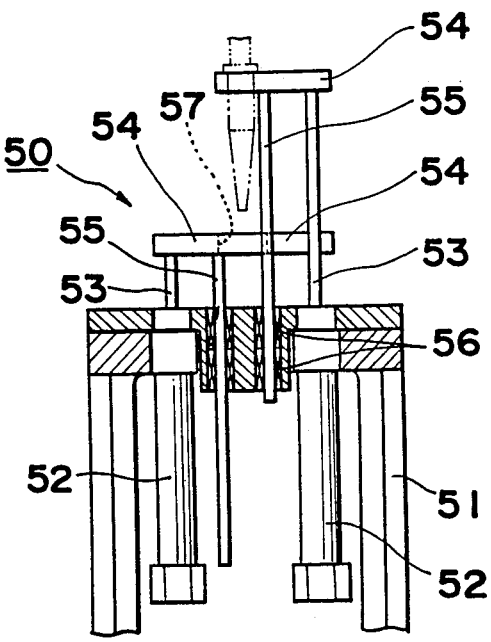
FIG. 9 is a partly broken side elevational view of the stopper mechanism of FIG. 8.

The pipet selection device further includes a stopper mechanism 50. As shown in FIGS. 8 and 9, the stopper mechanism 50 is constituted by a plurality of cylinders 52 fixed vertically to a frame 51, a cylinder shaft 53 extending from each of the cylinders 52, a stopper 54 secured to an upper end of the cylinder shaft 53 and a guide shaft 55 attached vertically to a lower face of a distal end portion of the stopper 54. The guide shaft 55 is guided by slide bearings 56 mounted in the frame 51. It is to be noted that each of the cylinders 52 can be replaced by a solenoid coil.

In the stopper mechanism 50, four cylinders 52 are spaced in the longitudinal direction of the base plate 21 from the remaining four cylinders 52 and the eight cylinders 52 are arranged in the sidewise direction of the slide plate 21 at an interval equal to a pitch of the wells a. A through-opening 57 for receiving the tip 43 is formed at the distal end portion of the stopper 54. Furthermore, the distal end portion of one stopper 54 protrudes in between those of the neighboring two stoppers 54 and the stoppers 54 longitudinally extend alternately oppositely in the longitudinal direction of the base plate 21 such that the through-openings 57 of the stoppers 54 are arranged in a line in the sidewise direction of the base plate 21.

In the case where exchange of the liquid is unnecessary at one of the 8 wells a of one column of the matrix in the sidewise direction of the culture tray A, the support member 25 of the horizontal displacement mechanism 23 is displaced to the stopper mechanism 50 where the stoppers 54 of the stopper mechanism 50 are individually adjusted in height. Namely, the stopper 54 for the pipet 22 corresponding to the well a not requiring exchange of the liquid is raised in height, while the remaining stoppers 54 are set at a low position as shown in FIG. 8 by way of example. On the other hand, in a state where the holding force of the pipet holding mechanism is lessened, the pipet holding mechanism as a whole is lowered to a predetermined position by the lifting mechanism 24. Thus, the tip 43 corresponding to the high stopper 54 is inserted into the through-opening 57 of the high stopper 54 and is prevented from being further lowered through contact of a flange portion 49 of the tip 43 with the high stopper 54. The remaining tips 43 are further lowered without their contact with the respective stoppers 54. In this state, the holding force of the pipet holding mechanism is increased. Consequently, a distal end of the tip 43 of the pipet 22 corresponding to the high stopper 54 is held higher than those of the remaining pipets 22 by the pipet holding mechanism. Subsequently, the support member 25 is slightly raised by the lifting mechanism 24 and then, is returned to a predetermined position by the horizontal displacement mechanism 23, so that it becomes possible to prevent the distal end of the unnecessary tip 43 from being inserted into the well a for exchange of the liquid.

Accordingly, by the pipet selection device of the above described arrangement, also in the case where one of the wells of one row or one column of the matrix has been subjected to a germicidal treatment due to mixing of germs thereinto, exchange of the liquid is not performed only at the specific well but is performed at the remaining wells of the row or the column of the matrix by the pipet selection mechanism at a time, thereby resulting in reduction of processing time of the dispensing machine.

Meanwhile, by the pipet selection device, also if a normal well does not require exchange of the liquid due to difference of progress of culture among the wells, unnecessary exchange of the liquid at the specific well can be prevented.

Furthermore, the pipet selection device is particularly useful for an automatic incubator in which progress of culture is measured at each of the wells.

FIGS. 10 to 16 show a tip exchange device which can be employed in the dispensing machine of the present invention. As shown in FIGS. 12 and 13, a pipet body 83 of each of the pipets 22 is secured to a support member 84 and a jig 62 is press fitted around a distal portion of the pipet body 83 such that a tip 61 of each of the pipets 22 is, in turn, fitted around a distal end portion of the jig 62. The jig 62 is formed by a rectilinear pipe made of stainless steel or the like and having a flange 63.

Figure 10:
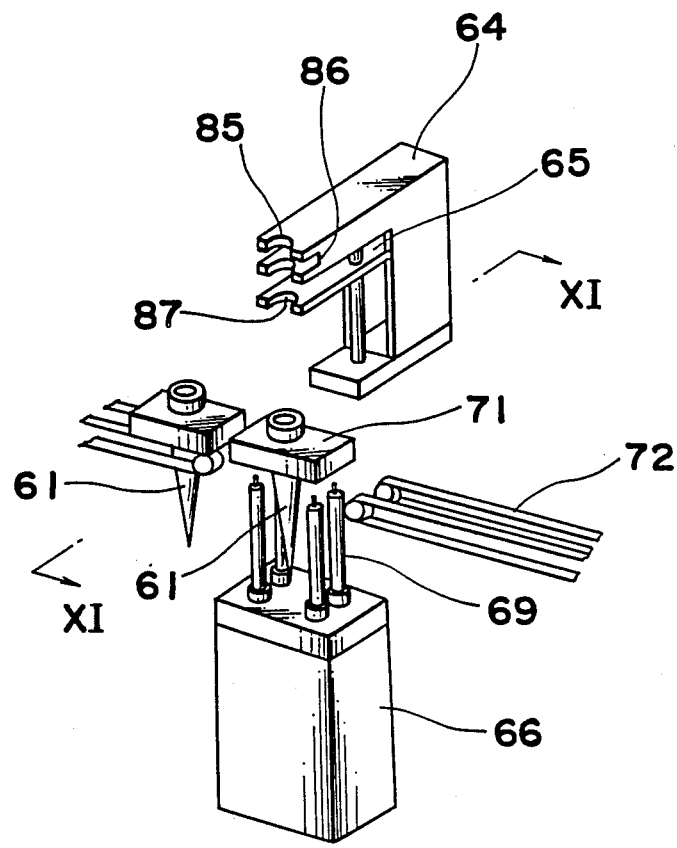
FIG. 10 is a perspective view of a tip exchange device employable in the dispensing machine of FIG. 2.
Figure 11:
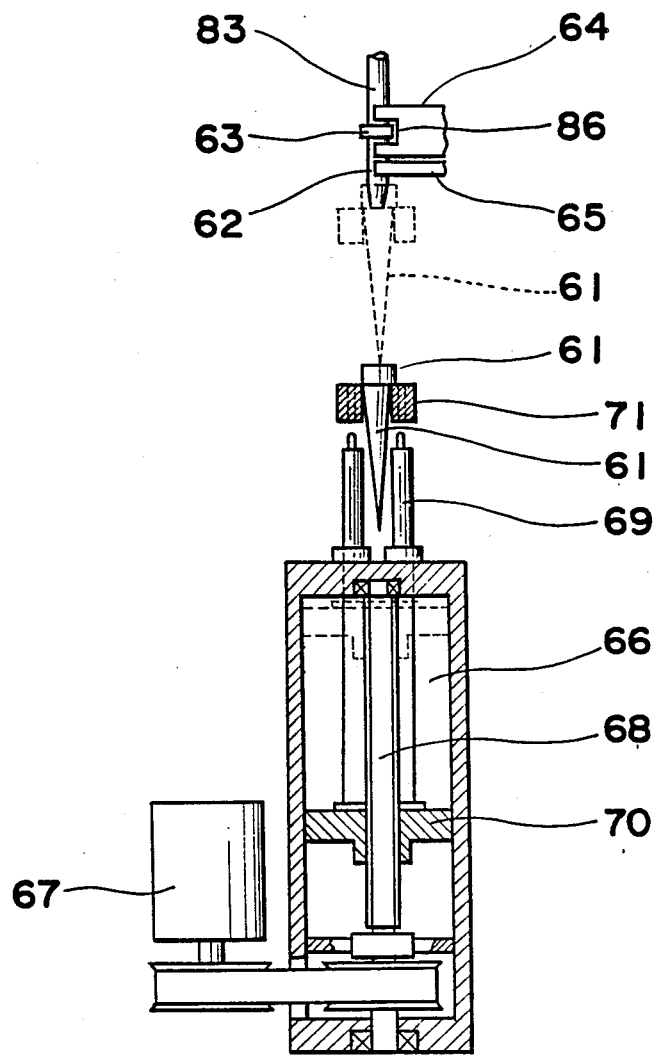
FIG. 11 is a sectional view taken along the line XI—XI in FIG. 10.

As shown in FIGS. 10 and 11, the tip exchange device includes a stopper mechanism 64 having a substantially U-shaped configuration, a tip depressing mechanism 65 and a tip lifting mechanism 66. The stopper mechanism 64 is formed, at its front end, with a semicircular recess 85 for fitting the jig 62 thereinto. When the jig 62 has been fitted into the recess 85, the flange 63 of the jig 62 is gripped in a groove 86 of the stopper mechanism 64 as shown in FIG. 11. The tip depressing mechanism 65 is formed by a plate formed, at its front end, with a recess 87. The tip depressing mechanism 65 is provided immediately below the stopper mechanism 64 and is driven upwardly and downwardly by a ball screw, etc. so as to depress the tip 61 downwardly. The tip lifting mechanism 66 includes a plate 70 in threaded engagement with a screw shaft 68 driven by a motor 67 and a tip magazine 71. Four poles 69 are mounted on the plate 70 so as to lift the tip magazine 71 through rotation of the screw shaft 68. The tip magazine 71 is formed with a hole for fitting the tip 61 thereinto and is transported to a predetermined position above the four poles 69 by a conveyor 72. A drive of the tip depressing mechanism 65 and the tip lifting mechanism 66 is not limited to the screw shaft. Thus, other mechanical devices and hydraulic or pneumatic cylinders can be, needless to say, employed for driving the tip depressing mechanism 65 and the tip lifting mechanism 66.

In order to perform exchange of the tip 61 by using the tip exchange device of the above described arrangement, the pipet body 83 is moved by the support member 84 and the jig 62 is fitted into the recess 85 of the stopper mechanism 64 such that the flange 63 of the jig 62 is gripped in the groove 86 of the stopper mechanism 64. Then, the tip depressing mechanism 65 is lowered so as to depress a flange portion of the tip 61 downwardly.

At this time, the flange 63 of the jig 62 is gripped in the groove 86 of the stopper mechanism 64 such that vertical movement of the jig 62 is prevented, so that the tip 61 is depressed downwardly so as to be detached from the jig 62. Hence, the used tip 61 is dropped down to the hole of the tip magazine 71. Another tip magazine 71 carrying a new tip 61 is transported to a position above the tip lifting mechanism 66 and then, is lifted by the poles 69 of the tip lifting mechanism 66. When the tip 61 is brought into contact with the distal end portion of the jig 62 as shown by the dotted lines of FIG. 11 so as to lift the jig 62. At this time, since vertical movement of the jig 62 is prevented by the stopper mechanism 64 through engagement of the flange 63 of the jig 62 with the groove 86 of the stopper mechanism 64, the tip 61 is press fitted around the distal end portion of the jig 62 so as to be secured to the jig 62. Thereafter, the poles 69 are lowered so as to return the empty pipet magazine 71 to the original position up to the conveyor 72 and the empty tip magazine 71 is held at the position until the next exchange of the tip 61. Thus, automatic exchange of the tip 61 can be performed.

By the tip exchange device of the above described arrangement, since forces applied to the pipet body 83 during exchange of the tip 61 are supported by the stopper mechanism 64, construction of the pipet body 83 may be designed in consideration of only a mechanism of displacement, etc. for exchange of the liquid and it is not necessary to increase rigidity or strength of the pipet body 83.

Figure 14:
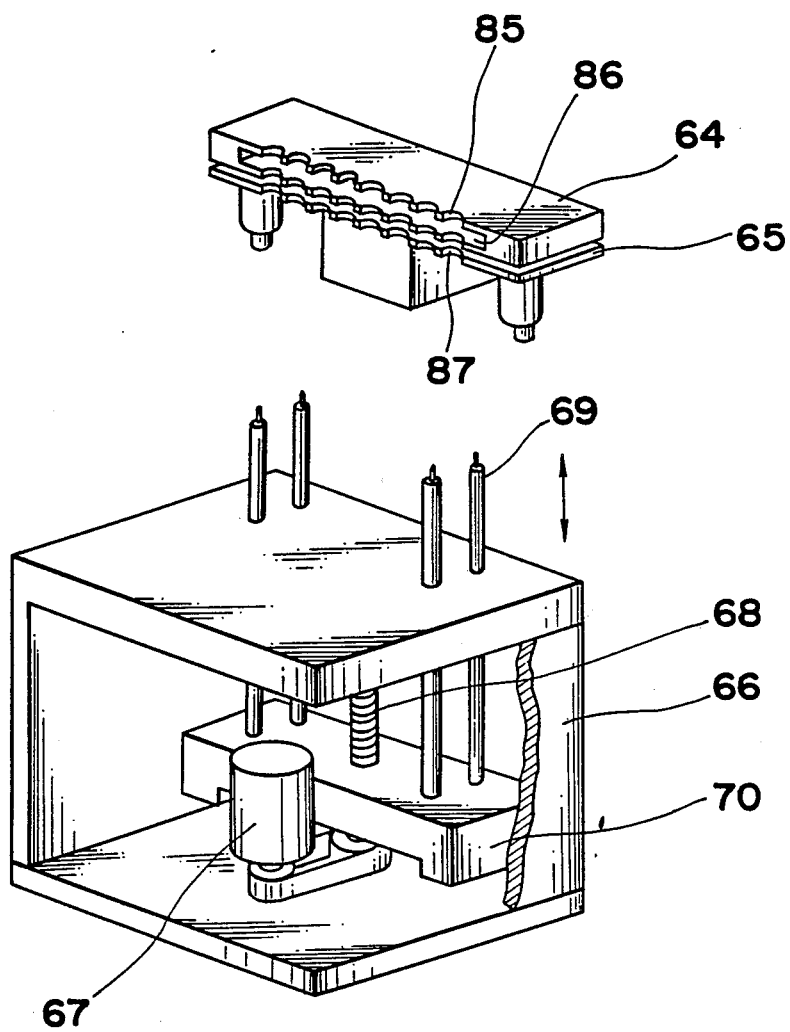
FIG. 14 is a perspective view of another tip exchange device.
Figure 15A:
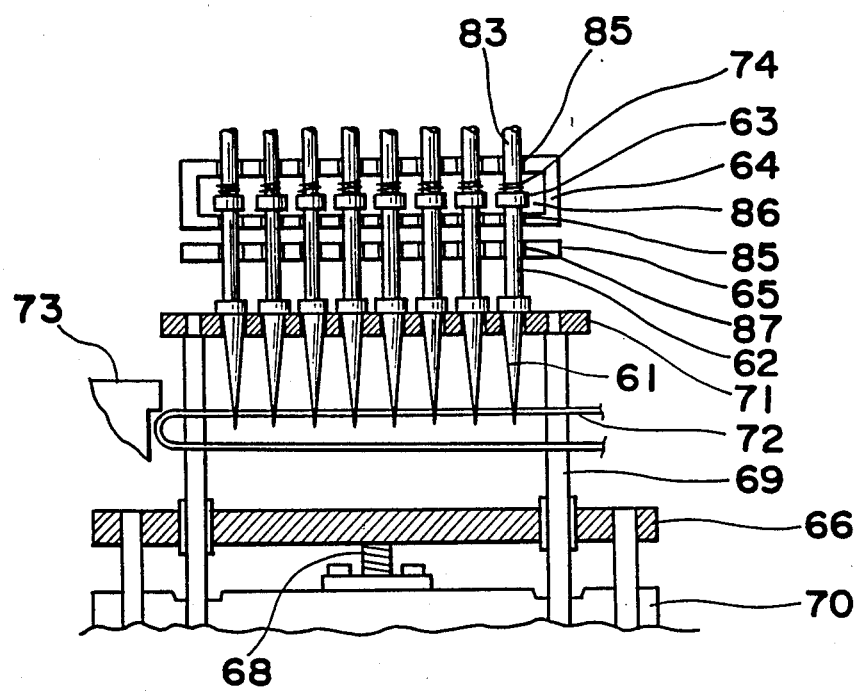
FIGS. 15a and 15b are partly sectional front elevational views showing two operational states of the tip exchange device of FIG. 14.
Figure 15B:
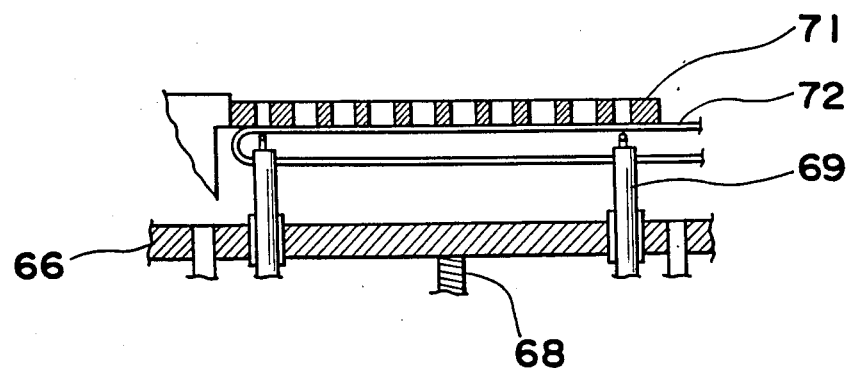
Figure 16:
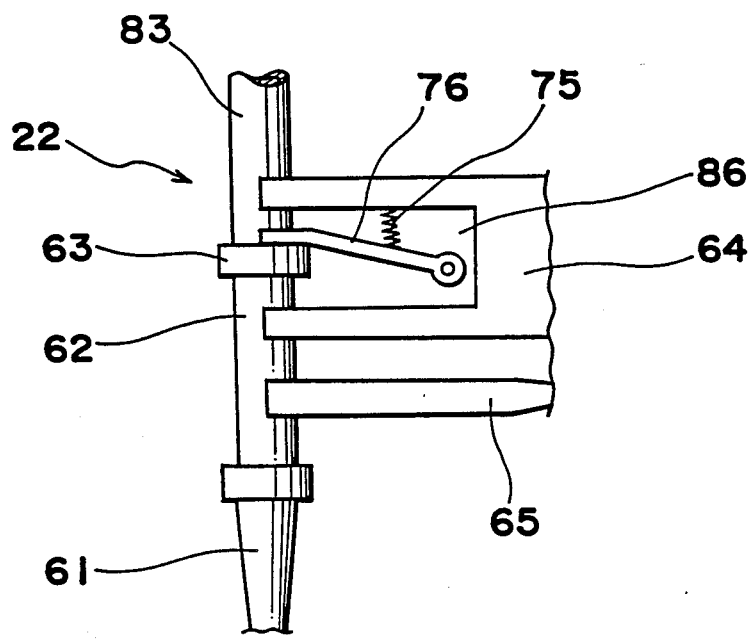
FIG. 16 is a side elevational view showing a modification of a stopper mechanism of the tip exchange device of FIG. 14.

FIGS. 14, 15a and 15b show a tip exchange device for performing exchange of a plurality of the tips 61 simultaneously. The tip exchange device includes the stopper mechanism 64, the tip depressing mechanism 65 and the tip lifting mechanism 66 as in the tip exchange device of FIG. 10. In this tip exchange device, the stopper mechanism 64 is formed with a plurality of the recesses 85 and the tip depressing mechanism 65 is formed with a plurality of the recesses 87. Meanwhile, the tip magazine 71 has a plurality of the holes for receiving a plurality of the tips 61. By using this tip exchange device, it becomes possible to simultaneously perform automatic exchange of a plurality of the tips 61 by the same operations as those of the tip exchange device of FIG. 10.

Meanwhile, a number of the tips 61 are used, the tips 61 are usually made of plastics. Usually, there is a considerable scatter in a diameter of a hole of the tip 61, which hole receives the jig 62. Therefore, such a phenomenon may take place that when a number of the tips 61 arranged horizontally are, respectively, pressed against the distal end portions of the jigs 62 having the flanges 63 arranged horizontally at a predetermined height by the stopper mechanism 64, the tips 61 are not fitted around the distal end portions of the jigs 62 uniformly, thereby resulting in detachment of some of the tips 61 from the corresponding jigs 62.

As shown in FIG. 15a, in order to obviate such a phenomenon, the groove 86 is so formed as to have a large width such that the flange 63 of each of the jigs 62 is loosely inserted into the groove 86 and a compression spring 74 having an inside diameter larger than that of the flange 63 and having an outside diameter smaller than that of the flange 63 is wound around the pipet body 83 in the groove 86. The compression spring 74 may be replaced by an arrangement of FIG. 16 in which the flange 63 is depressed downwardly by a pivotal lever 76 through a compression spring 75 attached to the stopper mechanism 64 and the pivotal lever 76. By provision of either the compression spring 74 or the compression spring 75 and the pivotal lever 76, when the tips 61 are lifted by the tip lifting mechanism 66, the tips 61 are, respectively, fitted around the distal end portions of the jigs 62 uniformly even if there is a scatter in the inside diameter of the tips 61, thereby eliminating the above described undesirable phenomenon.

Accordingly, by the tip exchange device, the tips can be exchanged automatically and an excessive force is not applied to the pipets. Therefore, rigidity of the pipet body is not required to be increased so greatly. Thus, since the tip exchange device can be designed in view of only positioning accuracy of the pipets relative to the wells, the dispensing machine can be manufactured at low cost and easily.

Although the present invention has been fully described by way of example with reference to the accompanying drawings, it is to be noted here that various changes and modifications will be apparent to those skilled in the art. Therefore, unless otherwise such changes and modifications depart from the scope of the present invention, they should be construed as being included therein.

What is claimed is:

1. A dispensing machine comprising:
   a syringe pump;
   a liquid tank;
   a pump displacement mechanism for displacing said syringe pump between said liquid tank and a container;
   a piston displacement mechanism for displacing a piston of said syringe pump;
   a weigher for measuring weights of said liquid tank and liquid in said liquid tank;
   a drainage system for draining the liquid of said liquid tank;
   a supply system for supplying the liquid to said liquid tank; and
   a control device which controls displacement of said syringe pump and said piston of said syringe pump and actuation of said supply system and said drainage system and reads measurement output signals of said weigher.

2. A dispensing machine as claimed in claim 1, wherein a plurality of wells filled with liquid are arranged in a matrix pattern on a culture tray corresponding to said liquid tank and a plurlity of pipets corresponding to said syringe pump are provided so as to correspond to the wells of one row or one column of the matrix such that said pipets are simultaneously displaced, for exchange of the liquid of the wells, relative to said culture tray at least in a vertical direction, said dispensing machine further including a pipet selection device for enabling selective use of said pipets, said pipet selection device comprising:
   a pipet support mechanism for adjustably supporting said pipets so as to allow individual positional adjustment of said pipets in the vertical direction; and
   a stopper mechanism for individually setting positions of distal ends of said pipets.

3. A dispensing machine as claimed in claim 2, wherein said stopper mechanism includes a plurality of stopper members each for supporting a flange portion of a tip attached to each of said pipets and a plurality of driving members of displacing said stopper members, respectively so as to individually set heights of said stopper members.

4. A dispensing machine as claimed in claim 1, wherein a plurality of wells filled with liquid are arranged in a matrix pattern on a culture tray corresponding to said liquid tank and at least one pipet corresponding to said syringe pump for exchanging the liquid of the wells is provided, said dispensing machine further including a tip exchange device for exchanging a tip attached, through a jig having a flange, to a distal end of said pipet, said tip exchange device comprising:
   a stopper means for securing said pipet through its engagement with said flange, which is formed with a first recess for receiving said jig;

5. A dispensing machine as claimed in claim 4, wherein said tip exchange device further includes an urging means for elastically urging downwardly said flange of said jig secured by said stopper means.

6. A dispensing machine as claimed in claim 2, further including a tip exchange device for exchanging a plurality of tips each attached, through a jig having a flange, to a distal end of each of said pipets, said tip exchange device comprising:
   a stopper means for securing said pipets through its engagement with said flanges, which is formed with a plurality of first recesses for receiving said jigs, respectively;
   a tip depressing means for depressing said tips downwardly, which is formed with a plurality of second recesses for receiving said jigs, respectively; and
   a tip lifting means for lifting a tip magazine carrying said tips.

7. A dispensing machine as claimed in claim 6, wherein said tip exchange device further includes an urging means for elastically urging downwardly said flanges of said jigs secured by said stopper means.

8. A dispensing machine as claimed in claim 3, further including a tip exchange device for exchanging a plurality of tips each attached, through a jig having a flange, to a distal end of each of said pipets, said tip exchange device comprising:
   a stopper means for securing said pipets through its engagement with said flanges, which is formed with a plurality of first recesses for receiving said jigs, respectively;
   a tip depressing means for depressing said tips downwardly, which is formed with a plurality of second recesses for receiving said jigs, respectively; and
   a tip lifting means for lifting a tip magazine carrying said tips.

9. A dispensing machine as claimed in claim 8, wherein said tip exchange device further includes an urging means for elastically urging downwardly said flanges of said jigs secured by said stopper means.

* * * * *